US008288151B2

(12) United States Patent
Aoyagi

(10) Patent No.: US 8,288,151 B2

(45) Date of Patent: Oct. 16, 2012

(54) BIOCHEMICAL REACTION CASSETTE

(75) Inventor: Takaaki Aoyagi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 150 days.

(21) Appl. No.: 11/449,609

(22) Filed: Jun. 9, 2006

(65) Prior Publication Data

US 2007/0004029 A1 Jan. 4, 2007

(30) Foreign Application Priority Data

Jun. 29, 2005 (JP) ................................ 2005-189910

(51) Int. Cl.
*C12M 1/36* (2006.01)
*C07H 21/04* (2006.01)

(52) U.S. Cl. ............... 435/283.1; 435/287.2; 435/287.9; 536/23.1

(58) Field of Classification Search ........................ None
See application file for complete search history.

(56) References Cited

U.S. PATENT DOCUMENTS

| | | | | |
|---|---|---|---|---|
| 5,726,026 A * | 3/1998 | Wilding et al. | .............. | 435/7.21 |
| 5,922,604 A * | 7/1999 | Stapleton et al. | ............... | 436/46 |
| 5,945,334 A | 8/1999 | Besemer et al. | ........... | 435/287.2 |
| 6,140,044 A | 10/2000 | Besemer et al. | .................. | 435/6 |
| 6,287,850 B1 | 9/2001 | Besemer et al. | ........... | 435/287.2 |
| 6,776,965 B2 | 8/2004 | Peters et al. | .................. | 422/100 |
| 7,204,139 B2 | 4/2007 | Takayama | .................. | 73/204.26 |
| 7,569,381 B2 * | 8/2009 | Aoyagi | ...................... | 435/287.2 |
| 2002/0086436 A1 * | 7/2002 | Buechler | ....................... | 436/164 |
| 2004/0037739 A1 * | 2/2004 | McNeely et al. | ............... | 422/58 |
| 2007/0059817 A1 | 3/2007 | Aoyagi | ...................... | 435/287.2 |
| 2007/0077645 A1 | 4/2007 | Aoyagi | ...................... | 435/287.2 |
| 2011/0028353 A1 * | 2/2011 | Aoyagi et al. | .................. | 506/39 |

FOREIGN PATENT DOCUMENTS

| | | |
|---|---|---|
| JP | 10-505410 | 5/1998 |
| JP | 2002-243748 | 8/2002 |
| JP | 2003-302399 | * 10/2003 |
| JP | 2004-93558 | 3/2004 |
| JP | 2004093558 | * 3/2004 |
| JP | 2005-30906 A | 2/2005 |

OTHER PUBLICATIONS

Official Action dated Mar. 12, 2010 in Chinese Application No. 200610100085.6.

* cited by examiner

*Primary Examiner* — Betty Forman

(74) *Attorney, Agent, or Firm* — Fitzpatrick, Cella, Harper & Scinto

(57) ABSTRACT

A biochemical reaction cassette is designed to uniformize the flow of liquid in the reaction chamber by using a simple additional arrangement. A member for reducing the cross sectional area of the flow channel that includes an injection port, a reaction chamber and a discharge port is arranged in the flow channel and a buffer room is provided.

14 Claims, 8 Drawing Sheets

BIOCHEMICAL REACTION CASSETTE

BACKGROUND OF THE INVENTION

1. Field of the Invention

This invention relates to a biochemical reaction cassette equipped with a probe carrier such as a DNA micro-array that can suitably be utilized when examining the presence or absence of one or more than one genes originating from pathogenic microbes in a specimen such as a blood specimen to determine the health condition of a subject of medical examination. More particularly, the present invention relates to the structure of a biochemical reaction cassette for making the flow rate of the liquid flowing at least in a reaction chamber uniform.

2. Related Background Art

Many proposals have been made for methods utilizing a hybridization reaction by using a probe carrier which may typically be a DNA micro-array in order to quickly and accurately analyze the base sequence of a nucleic acid or detect a target nucleic acid from a nucleic acid specimen. A DNA micro-array is formed by rigidly and highly densely immobilizing a probe having a complementary base sequence relative to that of a target nucleic acid on a solid phase such as a bead or a glass plate. An operation of detecting a target nucleic acid using a DNA micro-array generally includes the following steps.

In the first step, the target nucleic acid is amplified by means of an amplification method, which may typically be the PCR method. More specifically, firstly, first and second primers are added to a nucleic acid specimen and a thermal cycle is applied to it. The first primer specifically binds to part of the target nucleic acid while the second primer specifically binds to part of a nucleic acid that is complementary to the target nucleic acid. As a double-stranded nucleic acid containing the target nucleic acid binds to the first and second primers, the double-stranded nucleic acid containing the target nucleic acid is amplified by way of an extension reaction. After the double-stranded nucleic acid that contains the target nucleic acid is amplified to a sufficient extent, a third primer is added to the nucleic acid specimen and a thermal cycle is applied to it. The third primer is labeled with an enzyme, a fluorescent substance, a luminescent substance or the like and specifically binds to part of the nucleic acid that is complementary to the target nucleic acid. As the third primer binds to the nucleic acid that is complementary to the target nucleic acid, the target nucleic acid that is labeled with an enzyme, a fluorescent substance, a luminescent substance, or the like is amplified by way of an extension reaction. As a result, a labeled target nucleic acid is generated when the nucleic acid specimen contains the target nucleic acid, where no labeled target nucleic acid is generated when the nucleic acid specimen does not contain the target nucleic acid.

In the second step, the nucleic acid specimen is brought into contact with a DNA micro-array to cause a hybridization reaction to take place between the specimen and the probe of the DNA micro array. The probe and the target nucleic acid form a hybrid when the target nucleic acid that is complementary to the probe is contained in the nucleic acid specimen.

In the third step, the target nucleic acid is detected. It is possible to detect if the probe and the target nucleic acid form a hybrid by means of the labeling substance of the target nucleic acid. Thus, it is possible to see the presence or absence of a specific bas sequence.

DNA micro-arrays that are adapted to utilize a hybridization reaction are expected to find applications in the field of medical diagnosis for identifying pathogenic microbes and that of gene diagnosis for examining the genetic constitution of a patient. However, the steps of amplification of nucleic acid, hybridization and detection are mostly individually conducted by using separate devices. Hence the overall operation is a complex one and it takes time for diagnosis. Particularly, when a hybridization reaction is conducted on a slide glass, the probe can become defective and/or contaminated when the slide glass is touched by a finger because the specimen immobilizing surface is exposed. Therefore, DNA micro-arrays need to be handled with utmost care. For the purpose of eliminating the above described problems, proposals have been made for the structure of a biochemical reaction cassette in which a reaction chamber is provided with a DNA micro-array so as to be able to conduct a hybridization reaction in the reaction chamber and also a subsequent operation of detecting a hybrid.

Japanese Patent Application Laid-Open No. H10-505410 discloses a structure for forming a cavity and a method of manufacturing such a cavity. Japanese Patent Application Laid-Open No. 2003-302399 and Japanese Patent Application Laid-Open No. 2004-093558 disclose chamber structures for preventing air bubbles from remaining in the initial liquid filling stages. Japanese Patent Application Laid-Open No. 2002-243748 discloses a structure for uniformly spreading liquid and forming a flow of such liquid.

With structures of biochemical reaction cassettes as disclosed in the above-cited patent documents, the volume of the reaction chamber is as small as tens of several μL and the height of the reaction chamber is also small to show a flatly extending profile. Such a structure provides an advantage of requiring only a small amount of reagent or some other liquid and producing a laminar flow in the reaction chamber. Additionally, the liquid in the reaction chamber may be agitated to efficiently give rise to a hybridization reaction of a probe and a target nucleic acid on a solid phase. The simplest way of agitating the liquid may be pushing and pulling the liquid at the injection port and rocking the liquid in the reaction chamber.

FIGS. 11, 12A and 12B of the accompanying drawings illustrate a biochemical reaction cassette as an example. The illustrated biochemical reaction cassette comprises a substrate 111 and a casing 112. Assume that liquid is filled in the reaction chamber 103 of the biochemical reaction cassette 110. If more liquid is fed from the inject port 106 thereof, the liquid flow rate 122 at and near the center of the reaction chamber 103 becomes higher than the liquid flow rates 121 and 123 at and near the opposite ends of the reaction chamber 103. Therefore, as the liquid in the inside is pushed and pulled at the injection port 106 or the discharge port 107 to rock the liquid in the reaction chamber 103, the frequency at which the probe on the solid phase contacts the target nucleic acid is differentiated between at and near the center of the reaction chamber 103 and at and near the opposite ends of the reaction chamber 103. Additionally, washing liquid is made to flow in the reaction chamber 103 after the end of a hybridization reaction in order to remove the nucleic acid that remains in the inside without reacting. At this time again, the rate at which the unreacted nucleic acid is removed and the probability at which the target nucleic acid that has reacted with the probe on the solid phase is pulled off are differentiated because of the difference of flow rate between at and near the center of the reaction chamber 103 and at and near the opposite ends of the reaction chamber 103. As a result, the luminance can vary at different positions on the probe at the time of detection to adversely affect the diagnosis.

With the arrangement of Japanese Patent Application Laid-Open No. H10-505410, while a laminar flow takes place in a cavity, the problem of difference of flow rate between at and near the center of the cavity and at and near the opposite ends of the cavity is not dissolved. With the arrangements of Japanese Patent Application Laid-Open No. 2003-302399 and No. 2004-093558, while liquid uniformly spreads in the chamber in the initial liquid filling stages, the flow rate of liquid in the chamber is not uniformized when the chamber is filled with liquid. Finally, with the arrangement of Japanese Patent Application Laid-Open No. 2002-243748, the structure is inevitably complex and hence the reduction of cost of manufacturing such a cassette is limited.

SUMMARY OF THE INVENTION

In view of the above-identified circumstances, it is therefore the object of the present invention to provide a biochemical reaction cassette designed to uniformize the flow of liquid in the reaction chamber by using a simple additional arrangement.

In an aspect of the present invention, the above object is achieved by providing a biochemical reaction cassette comprising a flow channel including a reaction chamber having a region for immobilizing a probe for detecting a target nucleic acid, an injection port for injecting a specimen into the reaction chamber and a discharge port for discharging the specimen from the reaction chamber, the reaction chamber being adapted for bringing the specimen into contact with the probe immobilizing region to make the specimen react with the probe, the cassette further comprising a fluid resisting section provided in the flow channel including the injection port, the reaction chamber and the discharge port to reduce the cross section of the flow channel, the flow of fluid in the reaction chamber being controlled by the fluid resisting section.

In another aspect of the present invention, the above object is achieved by providing a biochemical reaction device comprising a flow channel including a reaction chamber having a region for immobilizing a probe for detecting a target nucleic acid, an injection port for injecting a specimen into the reaction chamber and a discharge port for discharging the specimen from the reaction chamber, the reaction chamber being adapted for bringing the specimen into contact with the probe immobilizing region to make the specimen react with the probe, the device further comprising a fluid resisting section provided in the flow channel including the injection port, the reaction chamber and the discharge port to reduce the cross section of the flow channel, the flow of fluid in the reaction chamber being controlled by the fluid resisting section.

In still another aspect of the present invention, there is provided a biochemical reaction cassette comprising a reaction chamber having a reaction site for a biochemical reaction, an injection port for injecting a specimen into the reaction chamber and a buffer room arranged between the injection port and the reaction chamber, the buffer room being adapted for controlling the flow rate of the specimen supplied to the reaction chamber.

In still another aspect of the present invention, there is provided a biochemical reaction device comprising a reaction chamber having a reaction site for a biochemical reaction, an injection port for injecting a specimen into the reaction chamber and a buffer room arranged between the injection port and the reaction chamber, the buffer room being adapted for controlling the flow rate of the specimen supplied to the reaction chamber.

Thus, according to the present invention, as a member for reducing the cross section of the flow channel including an injection port, a reaction chamber and a discharge port, or a buffer room, is arranged, the flow of fluid into the reaction chamber is controlled to make it possible to uniformize the flow rate in the reaction chamber. The fluid resisting member may be formed by means of a slot section where the ceiling is lower than the reaction chamber, a projection member from the ceiling, a pillar shaped member or a bulkhead member having a large number of through holes.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

Preferred embodiments of the present invention will now be described in detail in accordance with the accompanying drawings.

First Embodiment

Figure 1:
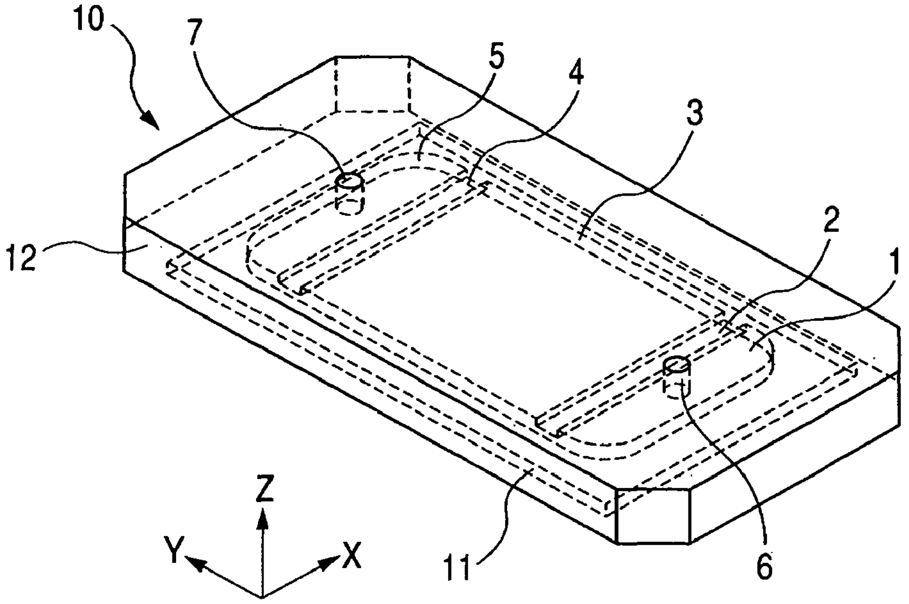
FIG. 1 is a schematic perspective view of the first embodiment of biochemical reaction cassette, illustrating the structure thereof.
Figure 2A:
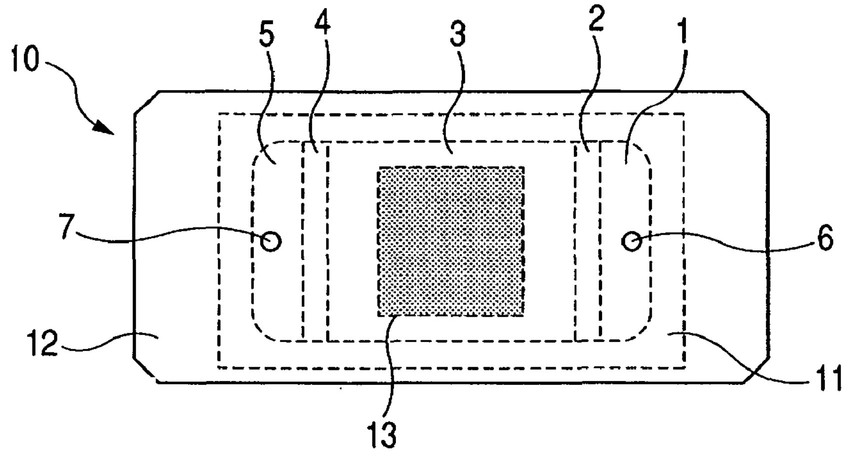
FIGS. 2A and 2B are a plan view and a cross sectional view of the first embodiment of biochemical reaction cassette, illustrating the structure thereof.
Figure 2B:
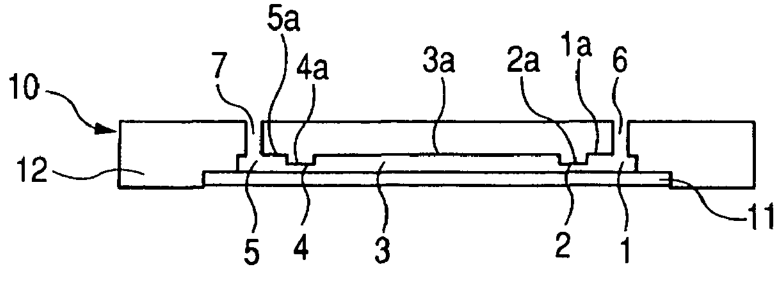
Figure 3A:
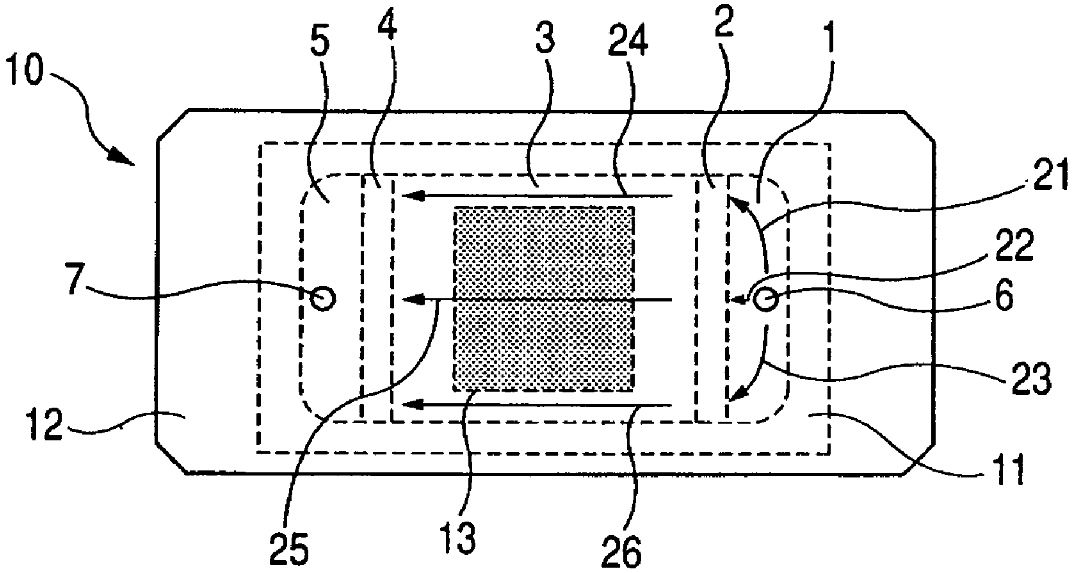
FIGS. 3A and 3B are plan views of the first embodiment of biochemical reaction cassette, illustrating the flow of liquid therein.
Figure 3B:
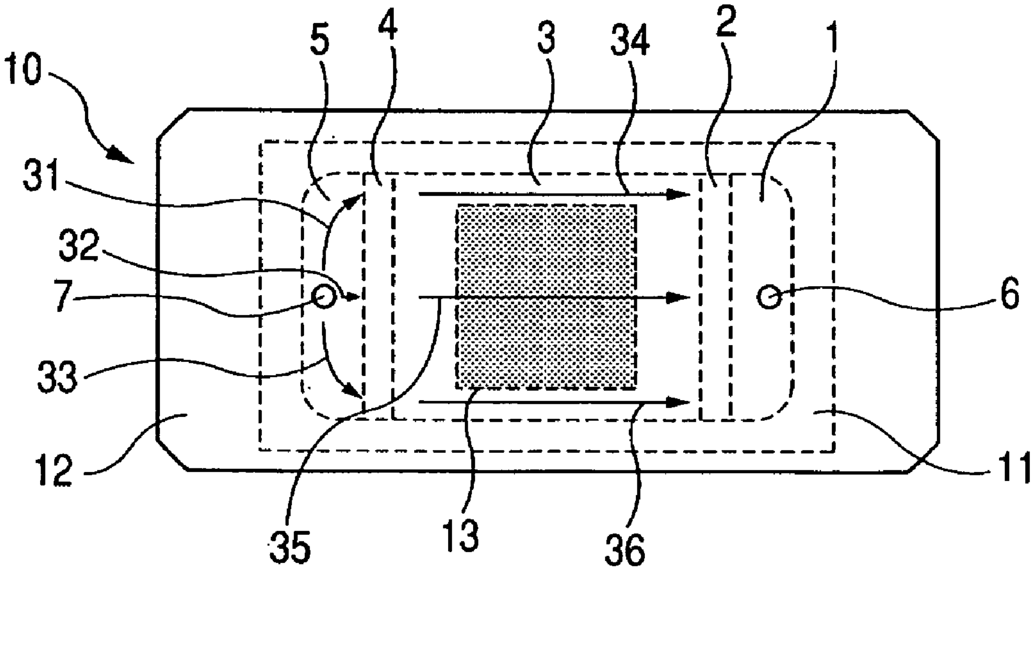

FIG. 1 is a schematic perspective view of the first embodiment of biochemical reaction device according to the present invention, which is a cassette type embodiment, illustrating the structure thereof. FIGS. 2A and 2B are a plan view and a cross sectional view of the first embodiment of biochemical reaction cassette, illustrating the structure thereof. FIGS. 3A and 3B are plan views of the first embodiment of biochemical reaction cassette, illustrating how liquid flows in the inside thereof.

Firstly, the structure of the cassette will be described. The cassette 10 comprises a glass substrate 11 and a casing 12 made of polycarbonate that are bonded to each other. The casing may be bonded to the substrate in various different ways including the illustrated one. The material of the casing 12 is not limited to polycarbonate and may alternatively be selected from plastics other than polycarbonate, glass, rubber, silicon rubber and composite materials of at least two of them. The casing 12 is provided with recesses having a predetermined cross section and arranged along the surface thereof to be bonded to the glass substrate 11 so that a first buffer room 1, a first slot section 2, a reaction chamber 3, a second slot section 4 and a second buffer room 5 are formed between the glass substrate 11 and the casing 12. The bottom surface of each of the spaces that are formed between the glass substrate 11 and the casing 12 and constitute the buffer rooms, the reaction chamber and the slot sections is formed by a part of the surface of the glass substrate 11. The bottom surfaces of the spaces are on the same level because the spaces constituting the buffer rooms, the reaction chamber and the slot sections are formed in the casing 12. However, some or all of the buffer rooms, the slot sections and the reaction chamber may be formed as so many recesses in the glass substrate 11 so that the bottoms of the spaces may not be on the same level.

With the arrangement illustrated in FIGS. 1, 2A and 2B, the slot sections that are formed by so many projecting members have respective ceilings 2*a* and 4*a* that are lower than the ceilings of the buffer rooms and the reaction chamber and upper parts of the slot sections operate as partitioning sections for the buffer rooms and the reaction chamber.

A probe immobilizing region 13 is provided on a part of the surface of the glass substrate 11 that operates as the bottom surface of the reaction chamber 3 so that, if the liquid filled in the reaction chamber 3 contains a target nucleic acid, the target nucleic acid and the probe in the probe immobilizing region 13 react with each other. An appropriate combination of a target nucleic acid and a probe may be selected according to the purpose of detection and both the target nucleic acid and the probe may be DNA.

Liquid is injected into the first buffer room 1 from the injection port 6 and passes sequentially through the first slot section 2, the reaction chamber 3, the second slot section 4 and the second buffer room 5 in the above mentioned order before it is discharged to the outside of the cassette 10 from the discharge port 7 connected to the second buffer room 5. In short, a liquid flow channel is formed by the above listed components.

When the dimensions of each of the spaces in FIG. 1 are expressed by coordinates of X (width)×Y (length)×Z (height, distance from bottom surface to ceiling section), the dimensions of the first buffer room 1 are 10×2×0.5 mm and those of the first slot section 2 are 10×1×0.1 mm, while those of the reaction chamber 3 are 10×10×0.5 mm. Additionally, the dimensions of the second slot section 4 are 10×1×0.1 mm and those of the second buffer room 5 are 10×2×0.5 mm. Note, however, that the dimensions of each of the spaces are not limited to those listed above and may take other values so long as the heights of the ceiling sections of the first slot section 2 and the second slot section 4 are lower than those of the first buffer room 1, the reaction chamber 3 and the second buffer room 5 and provide the intended functional features of the slots.

While the ceiling section of the reaction chamber 3 is flat and hence shows a constant height relative to the bottom surface (a constant height in the entire reaction chamber relative to the bottom surface as a reference level) in the above description, the profile of the ceiling section of the reaction chamber may be modified appropriately whenever necessary. Similarly, the profile of the ceiling section of each of the slot sections 2 and 4 may not necessarily be flat (and hence show a constant height in the entire slot section relative to the bottom surface as a reference level). In other words, it may be modified appropriately whenever necessary. However, from the viewpoint of simplifying the structure of the cassette and the process of manufacturing it, the illustrated structure represents a preferable mode of realization.

On the other hand, the heights of the ceiling sections 1*a*, 3*a* and 5*a* of the first buffer room 1, the reaction chamber 3 and the second buffer room 5 do not necessarily have to agree with each other. Similarly, the heights of the ceiling sections 2*a* and 4*a* of the first slot section 2 and the second slot section 4 do not necessarily have to agree with each other.

In the illustrated instance, the widths of the buffer rooms, the slot sections and the reaction chamber are the same as viewed in the direction of the flow channel (the length in the direction of the X-axis in FIG. 1). However, they do not necessarily have to be the same. Nevertheless, they are preferably made to agree with each other from the viewpoint of not complicating the manufacturing process and effectively achieving a uniform flow rate in the reaction chamber.

On the other hand, it is preferable from the viewpoint of achieving a uniform flow that the height of ceiling section of each of the buffer rooms is constant in the entire buffer room and the height of the ceiling section of the reaction chamber is constant in the entire reaction chamber as illustrated. This statement also applies to the second embodiment, which will be described hereinafter.

Now, a method of detecting a target nucleic acid by means of the embodiment of biochemical reaction cassette will be described below. Firstly, a nucleic acid specimen is prepared and, if necessary, the target nucleic acid is amplified by means of the above-described method. When the target nucleic acid exists in the nucleic acid specimen, a target nucleic acid labeled with a fluorescent substance is generated in the amplification process. While a fluorescent substance is used as labeling substance in the above description, it may replaced by a luminescent substance, an enzyme or the like. A solution of the nucleic acid specimen is injected into the cassette 10 from the injection port 6 with a liquid injection means (not shown). As the solution is filled in the first buffer room 1, the first slot section 2, the reaction chamber 3, the second slot section 4 and the second buffer room 5, it is heated to cause the hybridization reaction between the target nucleic acid in the solution and the probe on the probe immobilizing region 13 to progress. At this time, the solution is agitated in the reaction chamber 3 as it is driven to move back and forth under the temperature condition required for the hybridization reaction in order to increase the frequency at which the target nucleic acid in the solution contacts with the probe on the probe immobilizing region 13. Note that, the first buffer room 1, the first slot section 2, the reaction chamber 3, the second slot section 4 and the second buffer room 5 need to be always filled with the solution.

A flow as shown in FIG. 3A takes place when the solution of the nucleic acid specimen is fed from the side of the injection port 6 for agitation. If the liquid path does not provide any resistance, the solution flows from the injection port 6 toward the discharge port 7 substantially along a straight line. However, since the first slot section 2 resists the flow of solution, flows of the solution such as flows 21, 22 and 23 arise and the solution spreads all over the first buffer room 1. Then, as a result, the overall pressure of the first buffer room 1 rises and hence pressure is uniformly applied to the first slot section 2. The solution extruded from the first slot section 2 comes to show a uniform flow rate as indicated by 24, 25 and 26 in the reaction chamber 3. After feeding in the solution of the nucleic acid specimen from the injection port 6 by an amount required for agitation, the solution of the nucleic acid specimen is then fed in from the side of the discharge port 7. Like the instance of feeding the solution from the side of the injection port 6, a uniform flow rate as indicated by 34, 35 and 36 is produced for the same token in the reaction chamber 3 corresponding to the flows of the solution such as flows 31, 32 and 33 as shown in FIG. 3B. After feeding in the solution of the nucleic acid specimen from the discharge port 7 by an amount required for agitation, the solution of the nucleic acid specimen is then fed in from the side of the injection port 6 once again. Thereafter, the alternate feeding of solution from the discharge port 7 and from the injection port 6 is repeated to agitate the solution in the reaction chamber 3. Since a uniform flow rate is produced in the reaction chamber 3, any parts of the probe on the probe immobilizing region 13 have a same frequency of contacting the target nucleic acid in the nucleic acid specimen. In other words, the progress of the hybridization reaction does not show any difference due to positional difference on the probe immobilizing region 13.

The background level rises at the time of detection if the nucleic acid specimen remains, if partly, contained in the reaction chamber 3 or the nucleic acid specimen remains adhering to the wall surface of the reaction chamber 3. Therefore, such part of the nucleic acid specimen needs to be washed off. At the time of washing, washing liquid is made to flow from the injection port 6 for a predetermined period of time. At this time again, a uniform flow rate as indicated by 24, 25 and 26 in FIG. 3A is produced in the reaction chamber 3. Like the instance where a uniform flow rate of the solution of the nucleic acid specimen that is fed in at the time of agitation is produced, a uniform flow rate of the washing liquid is produced for the same token. As the washing liquid shows a uniform flow rate, the nucleic acid specimen adhering to the wall surface of the reaction chamber 3 is washed off to the same extent regardless of the position in the reaction chamber 3. Additionally, the target nucleic acid that binds to the probe may highly probably be peeled off by the flow of the washing liquid. However, if the target nucleic acid is partly peeled off from the probe immobilizing region, the probability at which the target nucleic acid is peeled off is the same at any area of the probe immobilizing region 13 because the flow rate of the washing liquid is uniform. Therefore, after the washing operation, it is possible to make the variance of fluorescence intensity smaller when the presence or absence of the target nucleic acid that is labeled by a fluorescent substance is detected by means of an optical system (not shown).

As described above in detail, as the solution and the washing liquid flowing in the reaction chamber 3 are made to produce a uniform flow rate, the target nucleic acid binds to the probe to the same ratio regardless of the position in the reaction chamber 3 to consequently improve the accuracy of detection.

Second Embodiment

Figure 4:
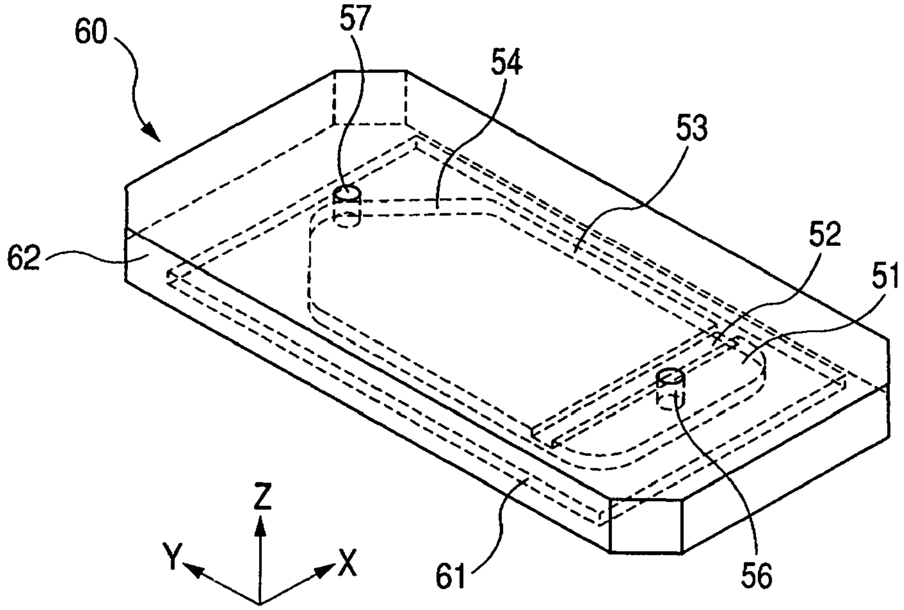
FIG. 4 is a schematic perspective view of the second embodiment of biochemical reaction cassette, illustrating the structure thereof.
Figure 5A:
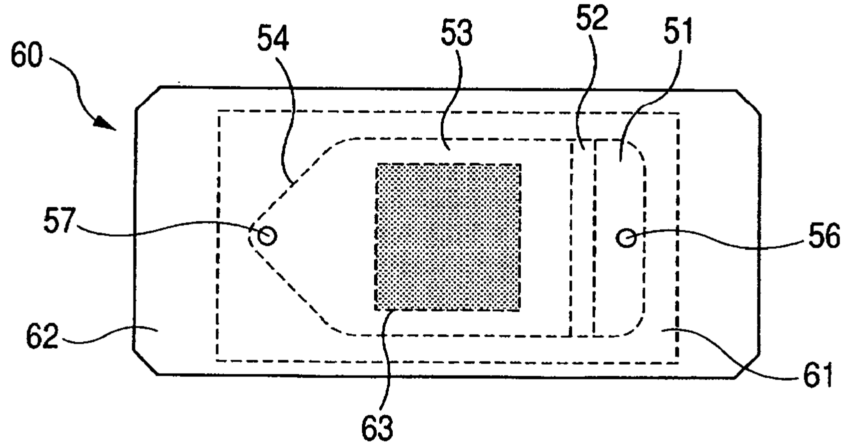
FIGS. 5A and 5B are a plan view and a cross sectional view of the second embodiment of biochemical reaction cassette, illustrating the structure thereof.
Figure 5B:
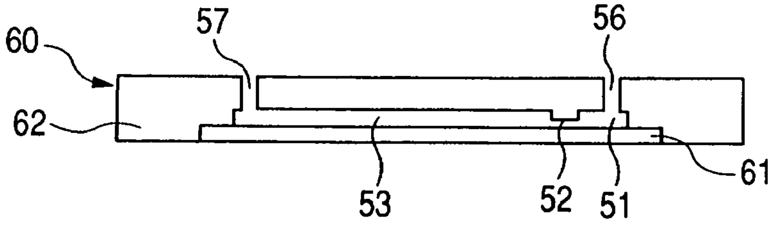
Figure 6A:
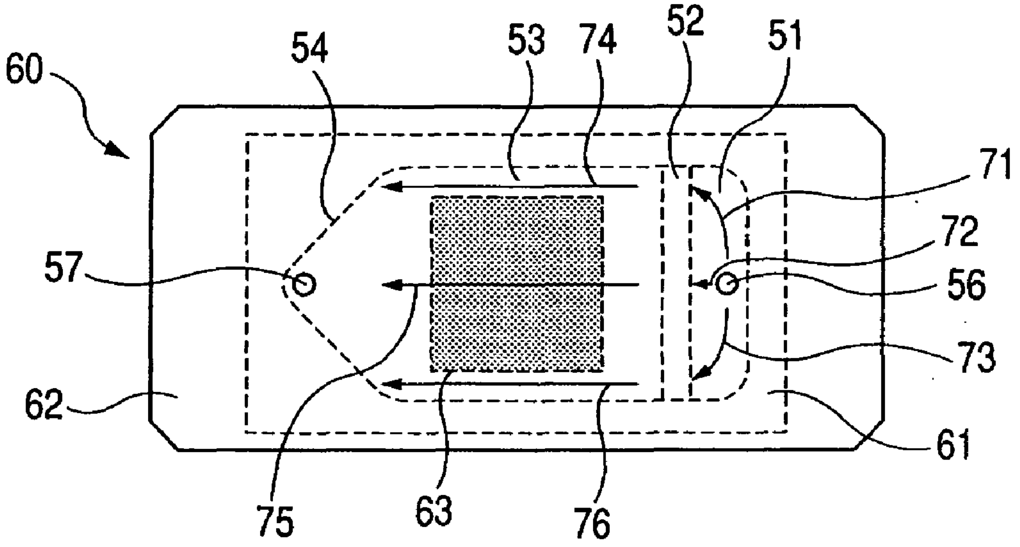
FIGS. 6A and 6B are plan views of the second embodiment of biochemical reaction cassette, illustrating the flow of liquid therein.
Figure 6B:
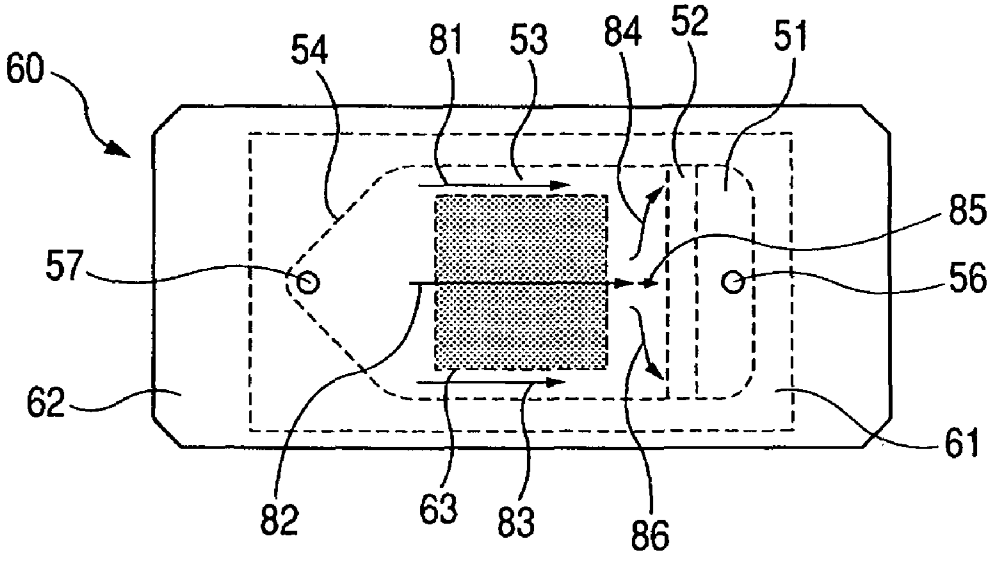

FIG. 4 is a schematic perspective view of the second embodiment of biochemical reaction cassette according to the present invention, illustrating the structure thereof. FIGS. 5A and 5B are a plan view and a cross sectional view of the second embodiment of biochemical reaction cassette, illustrating the structure thereof. FIGS. 6A and 6B are plan views of the second embodiment of biochemical reaction cassette, illustrating how liquid flows in the inside thereof.

Firstly, the structure of the cassette will be described. The cassette 60 comprises a glass substrate 61 and a casing 62 that are bonded to each other. The casing 62 is provided with recesses having a predetermined cross section and arranged along the surface thereof to be bonded to the glass substrate 61 so that a buffer room 51, a slot section 52, a reaction chamber 53 and a tapered section 54 are formed between the glass substrate 61 and the casing 62. The bottom surface of each of the spaces that constitute the buffer room, the reaction chamber, the slot section and the tapered section is formed by a part of the surface of the glass substrate 61. The bottom surfaces of the spaces are on the same level because the spaces constituting the buffer room, the reaction chamber and the slot section are formed as so many recesses in the casing 62. However, some or all of the buffer room, the slot section and the reaction chamber may be formed in the glass substrate 61 so that the bottoms of the spaces may not be on the same level.

The slot section 52 has a ceiling that is lower than the ceilings of the buffer room 51 and the reaction chamber 53 and upper part of the slot section 52 operates as partitioning section for the buffer room 51 and the reaction chamber 53.

A probe immobilizing region 63 is provided on a part of the surface of the glass substrate 61 that operates as the wall surface of the reaction chamber 53 so that the target nucleic acid contained in the solution filled in the reaction chamber 53 and the probe in the probe immobilizing region 63 react with each other. Liquid is injected into the buffer room 51 from the injection port 56 and passes sequentially through the slot section 52 and the reaction chamber 53 before it is discharged to the outside of the cassette 60 from the discharge port 57 connected to the reaction chamber 53. When the dimensions of each of the spaces are expressed by coordinates of X (width)×Y (length)×Z (height) as in the above description of the first embodiment, the dimensions of the buffer room 51 are 10×2×0.5 mm and those of the slot section 52 are 10×1×0.1 mm, while those of the reaction chamber 53 are 10×13×0.5 mm. Additionally, the tapered section 54 is inclined from the lateral wall surfaces of the reaction chamber 53 by 45° relative to the Y-direction. Note, however, that the dimensions of each of the spaces are not limited to those listed above and may take other values so long as the height of the slot section 52 is lower than those of the buffer room 51 and the reaction chamber 53 and provides the intended functional features of the slot. Additionally, the height of the buffer room 51 and that of the reaction chamber 53 do not have to agree with each other so long as they provide the intended functional features of them.

In the illustrated instance, the widths of the reaction chamber other than the tapered section, the buffer room, the slot section are the same as viewed in the direction of the flow channel. However, they do not necessarily have to be the same. Nevertheless, they are preferably made to agree with each other from the viewpoint of not complicating the manufacturing process and effectively achieving a uniform flow rate in the reaction chamber.

Now, a method of detecting a target nucleic acid by means of the embodiment of biochemical reaction cassette will be described below. Firstly, a nucleic acid specimen is prepared and, if necessary, the target nucleic acid is amplified by means of the above-described method. When the target nucleic acid exists in the nucleic acid specimen, a target nucleic acid labeled with a fluorescent substance is generated in the amplification process. While a fluorescent substance is used as labeling substance in the above description, it may replaced by a luminescent substance, an enzyme or the like. A solution of the nucleic acid specimen is injected into the cassette 60 from the injection port 56 with a liquid injection means (not shown). As the solution is filled in the first buffer room 51, the slot section 52 and the reaction chamber 53, it is heated to cause the hybridization reaction between the target nucleic acid in the solution and the probe on the probe immobilizing region 13 to progress. At this time, the solution is agitated in the reaction chamber 53 as it is driven to move back and forth under the temperature condition required for the hybridization reaction in order to increase the frequency at which the target nucleic acid in the solution contacts with the probe on the probe immobilizing region 63. Note that, the buffer room 51, the slot section 52 and the reaction chamber 53 need to be always filled with the solution. A flow as shown in FIG. 6A takes place when the solution of the nucleic acid specimen is fed from the side of the injection port 56 for agitation. If the liquid path does not provide any resistance, the solution flows from the injection port 56 toward the discharge port 57 substantially along a straight line. However, since the slot section 52 resists the flow of solution, flows of the solution such as flows 71, 72 and 73 arise and the solution spreads all over the first buffer room 51. Then, as a result, the overall pressure of the buffer room 51 rises and hence pressure is uniformly applied to the slot section 52. The solution extruded from the slot section 52 comes to show a uniform flow rate as indicated by 74, 75 and 76 in the reaction chamber 53. After feeding in the solution of the nucleic acid specimen from the injection port 56 by an amount required for agitation, the solution of the nucleic acid specimen is then fed in from the side of the discharge port 57. When the solution is fed in from the side of the discharge port 57, different flow rates appear in the reaction chamber 53 as indicated by 81, 82 and 83 in FIG. 6B because the slot section does not resist the flow of solution. Additionally, flows such as flows 84, 85 and 86 take place in front of the slot section 52.

After feeding in the solution of the nucleic acid specimen from the discharge port 57 by an amount required for agitation, the solution of the nucleic acid specimen is then fed in from the side of the injection port 56 once again. Thereafter, the alternate feeding of the solution from the discharge port 57 and from the injection port 56 is repeated to agitate the solution in the reaction chamber 53. The agitation efficiency in the reaction chamber 53 will be improved because the solution flows in different ways depending on the direction of feeding the solution. As a result, the distribution of concentration of the target nucleic acid in the solution filled in the reaction chamber 53 is always held to a constant level regardless of the position in the reaction chamber 53. In other words, the progress of the hybridization reaction does not show any difference due to positional difference on the probe immobilizing region 63.

The background level rises at the time of detection if the nucleic acid specimen remains, if partly, contained in the reaction chamber 53 or the nucleic acid specimen remains adhering to the wall surface of the reaction chamber 53. Therefore, such part of the nucleic acid specimen needs to be washed off. At the time of washing, washing liquid is made to flow from the injection port 56 for a predetermined period of time. At this time again, a uniform flow rate as indicated by 74, 75 and 76 in FIG. 6A is produced in the reaction chamber 53. Like the instance where a uniform flow rate of the solution of the nucleic acid specimen that is fed in from the side of the injection port 56 at the time of agitation is produced, a uniform flow rate of the washing liquid is produced for the same token. As the washing liquid shows a uniform flow rate, the nucleic acid specimen adhering to the wall surface of the reaction chamber 53 is washed off to the same extent regardless of the position in the reaction chamber 53. Additionally, the target nucleic acid that binds to the probe may highly probably be peeled off by the flow of the washing liquid. However, if the target nucleic acid is partly peeled off from the probe immobilizing region, the probability at which the target nucleic acid is peeled off is the same at any area of the probe immobilizing region 63 because the flow rate of the washing liquid is uniform. Therefore, after the washing operation, it is possible to make the variance of fluorescence intensity smaller when the presence or absence of the target nucleic acid that is labeled by a fluorescent substance is detected by means of an optical system (not shown).

Liquid flows differently in the reaction chamber 53 of the second embodiment depending on the direction of the flow of liquid so that the efficiency of agitating the target nucleic acid is improved in the reaction chamber 53 and the progress of hybridization reaction is held to a constant level regardless of the position in the reaction chamber 53. Additionally, since the washing liquid flows at a same flow rate, the target nucleic acid is washed off to a same extent regardless of the position in the reaction chamber 53 to improve the detection accuracy.

As described above in detail by way of the first embodiment and the second embodiment, it is possible to suppress the variances of flow rate in the reaction chamber when liquid is made to flow from the injection port toward the discharge port as a result of providing at least a buffer room at the upstream side of the reaction chamber with a slot section interposed between them. In other words, it is possible to supply a liquid specimen uniformly to the probe region. More specifically, when liquid is made to flow from the injection port to the discharge port under a condition where the buffer room, the slot section and the reaction chamber are filled with liquid, the liquid supplied to the buffer room tends to spread and flow all over the buffer room because the slot section resists the liquid flow. Then, as a result, the pressure in the buffer room rises to extrude the liquid from the slot section toward the reaction chamber. At this time, the power of the pressure in the buffer room extruding the liquid from the slot section is uniformly distributed in the transversal direction of the slot section so that liquid flows at a uniform flow rate in the reaction chamber.

On the other hand, when a buffer room is also provided at the downstream side of the reaction chamber with a slot section interposed between them in addition to the upstream side, the flow rate of liquid in the reaction chamber is also uniformized when the liquid is rocked for the purpose of agitation.

Meanwhile, when a buffer room is provided only at the upstream side of the reaction chamber with a slot section interposed between them (and hence neither a buffer room nor a slot section is provided at the downstream side), liquid flows at a uniform flow rate when it is made to flow from the injection port for the above described reason. However, liquid flows at different flow rates in the transversal direction when it is made to flow from the discharge port. Therefore, when the liquid is rocked for the purpose of agitation, it flows differently in the forward direction and in the backward direction to consequently improve the agitation efficiency in the reaction chamber.

With either of the above described arrangements, it is possible to provide a biochemical reaction cassette with an improved uniformity of flow rate and an improved efficiency of agitation due to the effect of one or more than one slot sections, the cassette having a volume for securing liquid necessary for the buffer room and the reaction chamber.

While the one or more than one slot sections of the first embodiment and the second embodiment described above are made to have a ceiling section lower than both that of the buffer room and that of the reaction chamber to form a low profile flow channel, it is also possible to form a partitioning section having the functional feature of a slot section by arranging a projection that projects downward from the ceiling section toward the bottom surface with a predetermined gap secured between the front end thereof and the bottom surface and extends across the entire width of the ceiling section.

Third Embodiment

Figure 7:
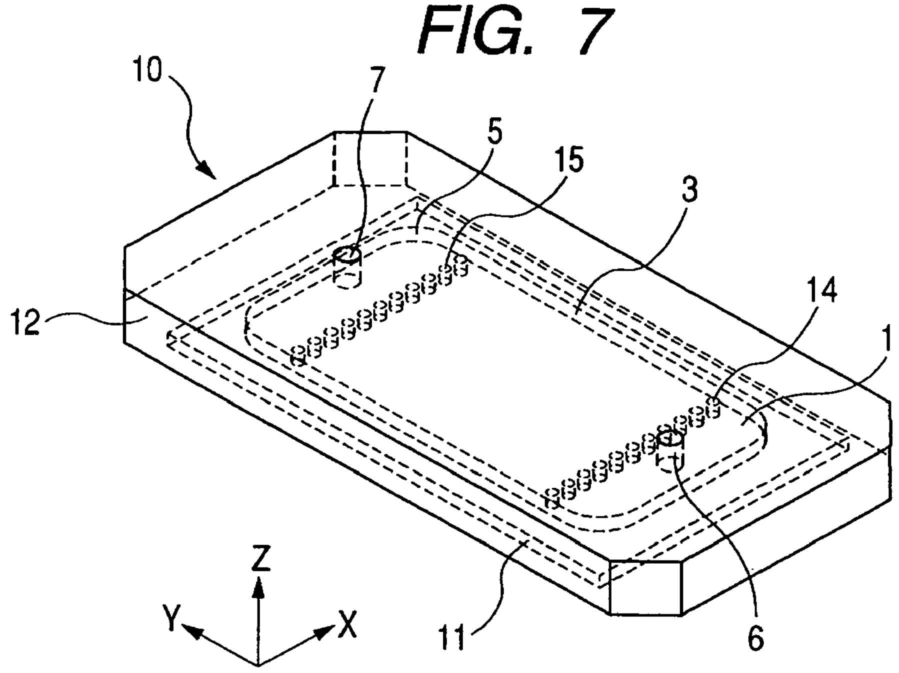
FIG. 7 is a schematic perspective view of the third embodiment of biochemical reaction cassette, illustrating the structure thereof.
Figure 8A:
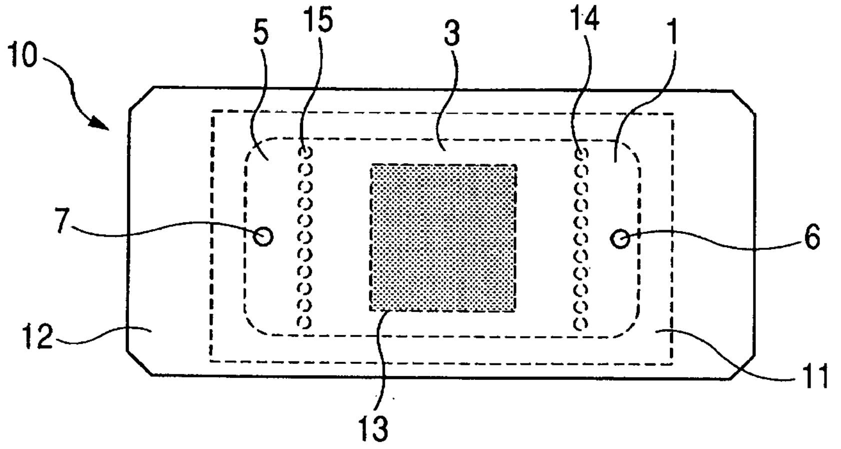
FIGS. 8A and 8B are a plan view and a cross sectional view of the third embodiment of biochemical reaction cassette, illustrating the structure thereof.
Figure 8B:
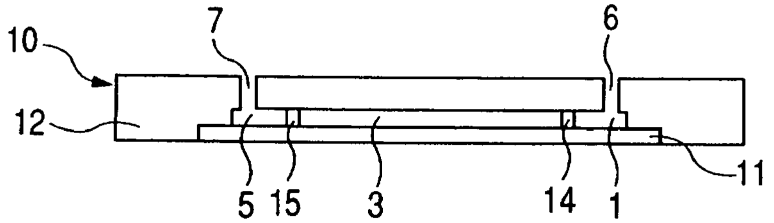

FIG. 7 is a schematic perspective view of the third embodiment of biochemical reaction cassette, illustrating the structure thereof. FIGS. 8A and 8B are a plan view and a cross sectional view of the third embodiment of biochemical reaction cassette, illustrating the structure thereof.

The cassette has a structure realized by modifying the first embodiment in such a way that first pillar shaped members 14 and second pillar-shaped members 15 are used respectively for the first slot section 2 and the second slot section 4. Liquid flows through the gaps formed by the first pillar-shaped members 14 and those formed by the second pillar-shaped members 15. Otherwise, this embodiment has the same structure as that of the first embodiment.

Figure 11:
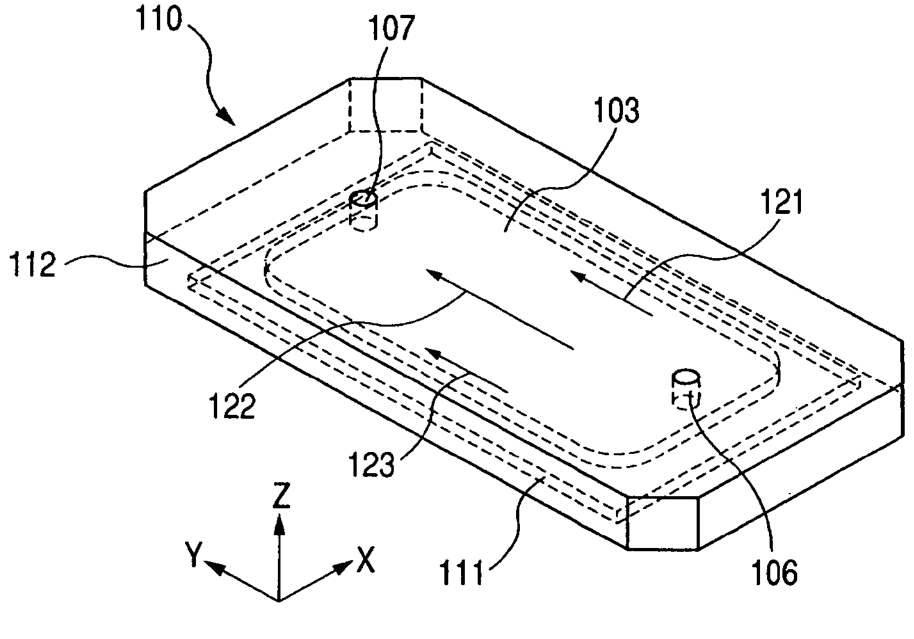
FIG. 11 is a schematic perspective view of a known biochemical reaction cassette, illustrating the structure thereof.
Figure 12A:
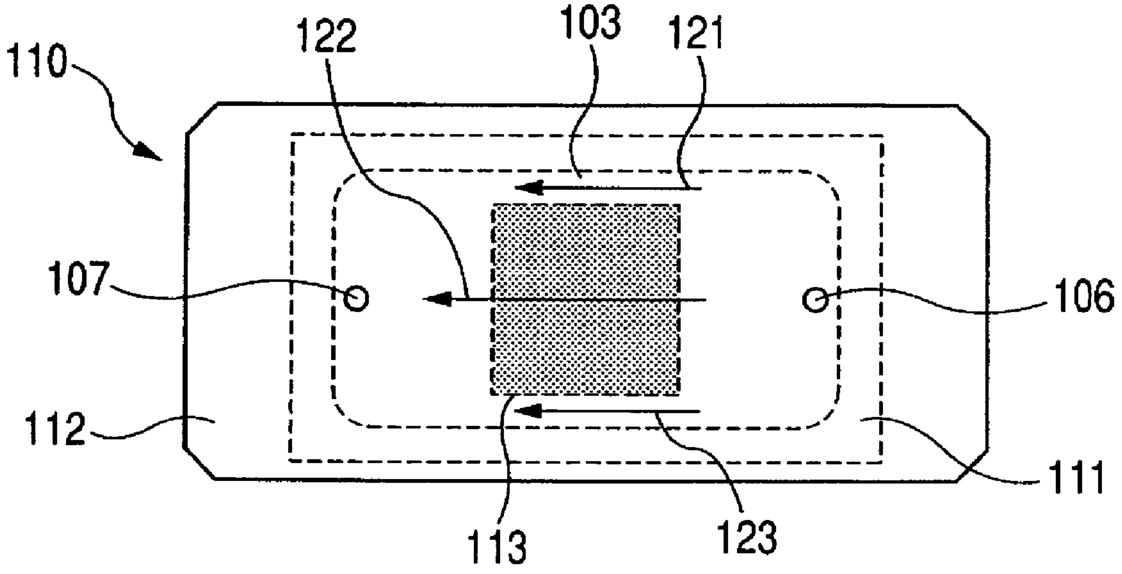
FIGS. 12A and 12B are a plan view and a cross sectional view of the known biochemical reaction cassette, illustrating the structure thereof.
Figure 12B:
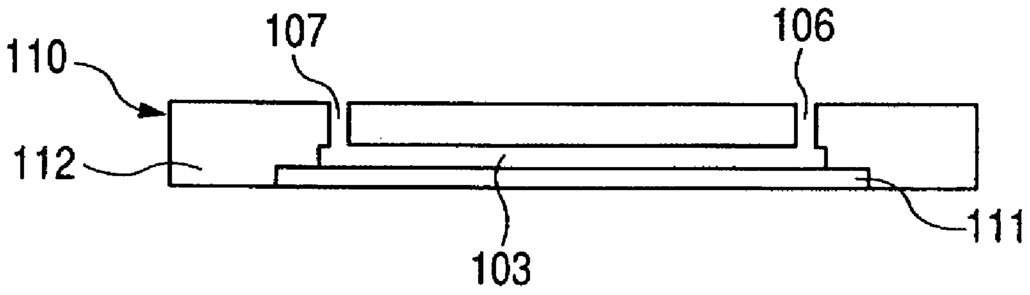

A cassette of this embodiment is manufactured by integrally molding a casing 12. Note, however, the method of manufacturing a cassette of this embodiment is not limited to the above described one and alternatively the first pillar-shaped members 14 and the second pillar-shaped members 15 may be bonded to the casing 112 illustrated in FIGS. 11, 12A and 12B. In FIG. 12A, reference numeral 113 denotes a probe immobilizing region.

With the above described arrangement, the first pillar-shaped members 14 and the second pillar-shaped members 15 reduce the cross section of the flow channel to provide effects similar to those of the first slot section 2 and the second slot section 4 of the first embodiment. In other words, as the solution of the nucleic acid specimen and the washing liquid flowing in the reaction chamber 3 are made to produce a uniform flow rate, the target nucleic acid binds to the probe to the same ratio regardless of the position in the reaction chamber 3 to consequently improve the accuracy of detection.

Fourth Embodiment

Figure 9A:
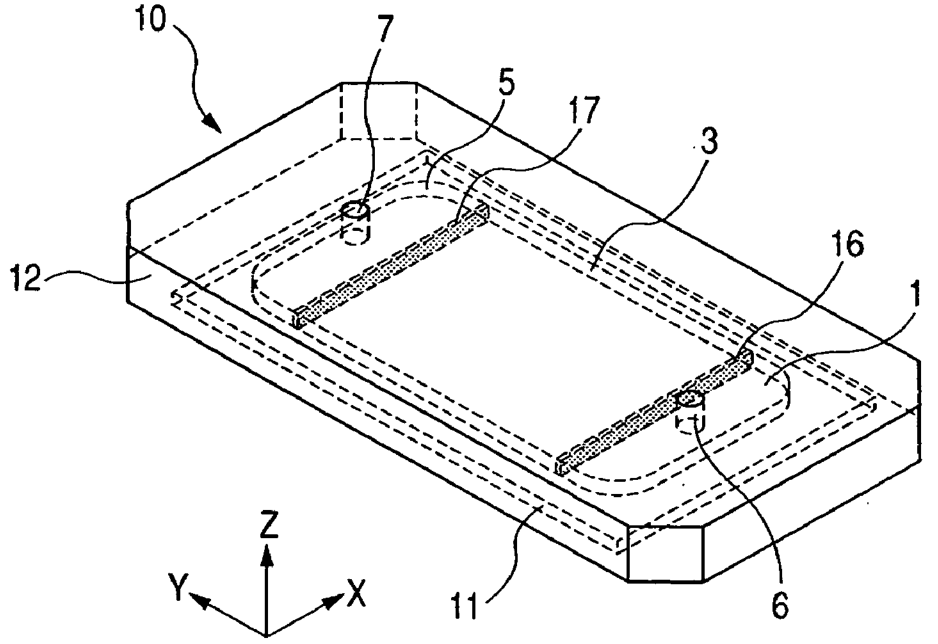
FIGS. 9A and 9B are schematic perspective views of the fourth embodiment of biochemical reaction cassette, illustrating the structure thereof.
Figure 10A:
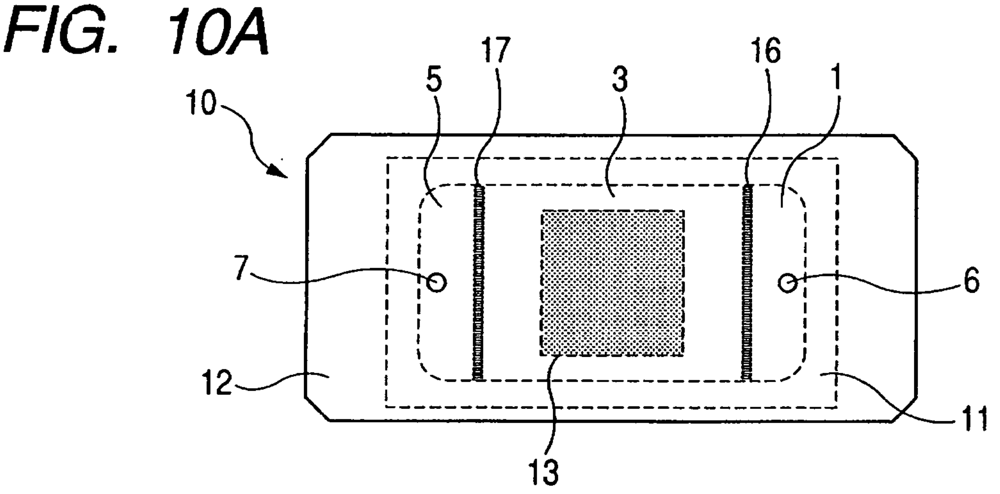
FIGS. 10A and 10B are a plan view and a cross sectional view of the fourth embodiment of biochemical reaction cassette, illustrating the structure thereof.
Figure 10B:
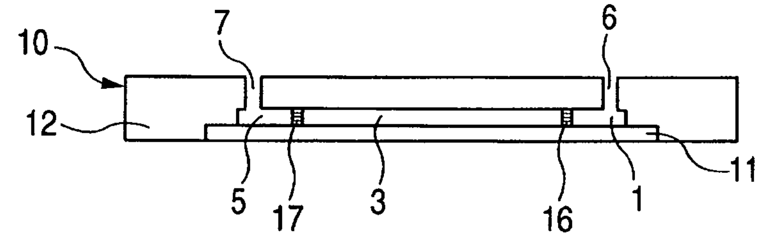

FIG. 9A is a schematic perspective view of the fourth embodiment of biochemical reaction cassette, illustrating the structure thereof. FIGS. 10A and 10B are a plan view and a cross sectional view of the fourth embodiment of biochemical reaction cassette, illustrating the structure thereof.

The cassette has a structure realized by modifying the first embodiment in such a way that a first bulkhead member 16 and a second bulkhead member 17 are used respectively for the first slot section 2 and the second slot section 4. The first bulkhead member 16 and the second bulkhead member 17 are provided with a large number of through holes for allowing liquid to flow through them in the Y-direction illustrated in FIG. 9A. Otherwise, this embodiment has the same structure as that of the first embodiment.

Figure 9B:
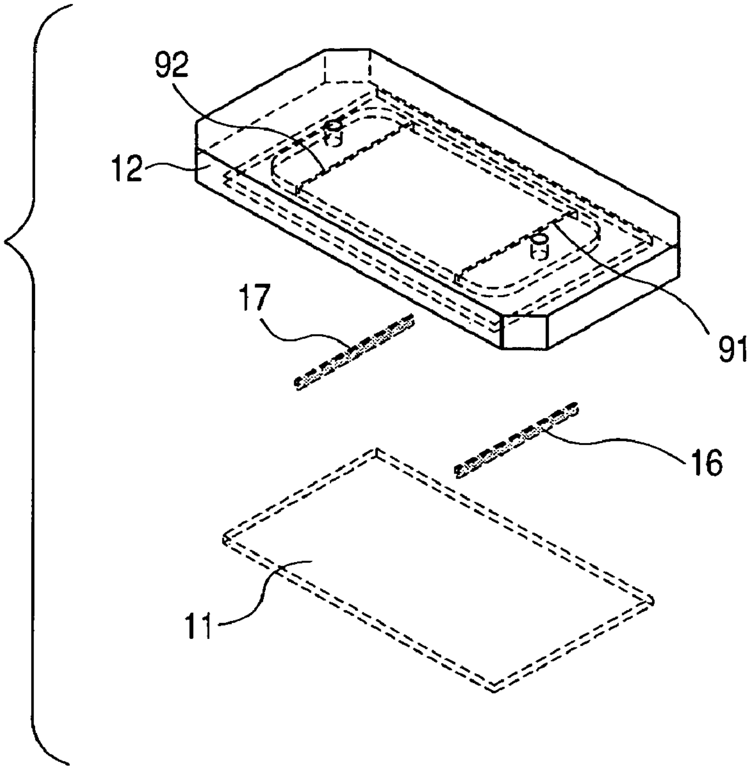

FIG. 9B illustrates a method of manufacturing a cassette of this embodiment. The casing 12 is provided with groove sections 91 and 92 and the first bulkhead member 16 and the second bulkhead member 17 are fitted respectively into the groove sections 91 and 92 and pinched by the casing 12 and the glass substrate 11. Note, however, the method of manufacturing a cassette of this embodiment is not limited to the above described one and alternatively the first bulkhead member 16 and the second bulkhead member 17 may be rigidly bonded to the casing 112 illustrated in FIGS. 11, 12A and 12B.

With the above described arrangement, the first bulkhead member 16 and the second bulkhead member 17 reduce the cross section of the flow channel to provide effects similar to those of the first slot section 2 and the second slot section 4 of the first embodiment. In other words, as the solution of the nucleic acid specimen and the washing liquid flowing in the reaction chamber 3 are made to produce a uniform flow rate, the target nucleic acid binds to the probe to the same ratio regardless of the position in the reaction chamber 3 to consequently improve the accuracy of detection.

The present invention is not limited to the above embodiments and various changes and modifications can be made within the spirit and scope of the present invention. Therefore, to apprise the public of the scope of the present invention, the following claims are made.

This application claims priority from Japanese Patent Application No. 2005-189910 filed on Jun. 29, 2005, which is hereby incorporated by reference herein.

What is claimed is:

1. A biochemical reaction cassette comprising a substrate having a planar surface and a casing having a recess, the substrate and the casing being bonded to each other such that the planar surface and the recess face each other to form a flow channel having a cross section perpendicular to a flow direction in the flow channel as a space between the substrate and the casing, the flow channel including a reaction chamber for reacting therein a target nucleic acid with a probe for detecting the target nucleic acid, an injection port for injecting a specimen potentially containing the target nucleic acid into the reaction chamber and a discharge port for discharging the specimen from the reaction chamber, the flow channel further including a buffer room provided between the injection port and the reaction chamber and a fluid resisting section provided as a projection member formed between the buffer room and the reaction chamber in the recess, the fluid resisting section exhibiting a higher flow resistance as compared with any of the reaction chamber and the buffer room, the fluid resisting section being provided on both the upstream and downstream sides of the reaction chamber.

2. The cassette according to claim 1, wherein the reaction chamber has a uniform height between the planar surface of the substrate and a surface of the recess over the entire area of the reaction chamber.

3. The cassette according to claim 1, wherein the projection member is formed of pillar-shaped members arranged between the buffer room and the reaction chamber.

4. The cassette according to claim 1, wherein the projection member is a bulkhead provided with micro-pores.

5. The cassette according to claim 1, wherein the fluid resisting section is a slot section formed by arranging a partition extending vertically from a surface of the recess and/or the planar surface of the substrate, the buffer room being arranged adjacent to and separated from the reaction chamber.

6. The cassette according to claim 5, wherein the slot section has a height that is uniform over the entire area of the slot section.

7. The cassette according to claim 5, wherein the partition is arranged in the flow channel so as to separate the reaction chamber and the buffer room in the flow channel.

8. The cassette according to claim 5, wherein the buffer room and the slot section have the same width as the reaction chamber relative to the flow direction.

9. The cassette according to claim 5, wherein the buffer room has the injection port.

10. The cassette according to claim 5, wherein the reaction chamber has the discharge port and is tapered toward the discharge port in terms of width.

11. The cassette according to claim 10, wherein the buffer room has the injection port.

12. The cassette according to claim 1, wherein the buffer room and the fluid resisting section have the same width as the reaction chamber.

13. The cassette according to claim 1, wherein the buffer room has a length along the flow direction and a width perpendicular to the flow direction, the width being larger than the length.

14. A biochemical reaction device formed by bonding a substrate having a planar surface and a casing having a recess such that the planar surface and the recess face each other, comprising as spaces between the substrate and the casing:

a reaction chamber having therein a reaction site for a biochemical reaction;

an injection port for injecting a specimen into the reaction chamber; and a buffer room provided between the injection port and the reaction chamber, the device further comprising a projection member provided between the buffer room and the reaction chamber in the recess so as to raise a flow resistance for a fluid flowing between the buffer room and the reaction chamber, the projection member being provided on both the upstream and downstream sides of the reaction chamber.

* * * * *